United States Patent
Moly et al.

(10) Patent No.: US 12,248,628 B2
(45) Date of Patent: Mar. 11, 2025

(54) ITERATIVE CALIBRATION METHOD FOR A DIRECT NEURAL INTERFACE USING A MARKOV MIXTURE OF EXPERTS WITH MULTIVARIATE REGRESSION

(71) Applicant: COMMISSARIAT A L'ENERGIE ATOMIQUE ET AUX ENERGIES ALTERNATIVES, Paris (FR)

(72) Inventors: Alexandre Moly, Grenoble (FR); Tetiana Aksenova, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 1035 days.

(21) Appl. No.: 17/011,276

(22) Filed: Sep. 3, 2020

(65) Prior Publication Data

US 2021/0064942 A1 Mar. 4, 2021

(30) Foreign Application Priority Data

Sep. 4, 2019 (FR) ..................................... 19 09706

(51) Int. Cl.
*G06N 20/00* (2019.01)
*A61B 5/30* (2021.01)
(Continued)

(52) U.S. Cl.
CPC ................ *G06F 3/015* (2013.01); *A61B 5/30* (2021.01); *A61B 5/316* (2021.01);
(Continued)

(58) Field of Classification Search
CPC .... G06F 3/015; G06F 18/2113; G06F 18/214; G06F 18/295; G06F 3/038; A61B 5/30;
(Continued)

(56) References Cited

U.S. PATENT DOCUMENTS

2018/0005105 A1   1/2018  Schaeffer et al.
2019/0201691 A1*  7/2019  Poltorak ................. A61B 5/165
2019/0320924 A1  10/2019  Yelisyeyev

FOREIGN PATENT DOCUMENTS

FR   3 046 471 A1   7/2017
FR   3 053 495 A1   1/2018
FR   3 061 318 A1   6/2018

OTHER PUBLICATIONS

Schaeffer ("Switching Markov decoders for asynchronous trajectory reconstruction from ECoG signals in monkeys for BCI applications") Journal of Physiology-Paris vol. 110, Issue 4, Part A, Nov. 2016, pp. 348-360 (Year: 2016).*

Eliseyev ("Recursive exponentially weighted n-way partial least squares regression with recursive-validation of hyper-parameters in brain-computer interface applications") SCientifiC REPOrTS | 7: 16281 | DOI:10.1038/s41598-017-16579-9 (Year: 2017).*

(Continued)

*Primary Examiner* — Michael W Ayers
*Assistant Examiner* — Su-Ting Chuang
(74) *Attorney, Agent, or Firm* — Oblon, McClelland, Maier & Neustadt, L.L.P.

(57) ABSTRACT

This invention relates to a method of calibrating a direct neural interface with continuous coding. The observation variable is modelled by an HMM model and the control variable is estimated by means of a Markov mixture of experts, each expert being associated with a state of the model.

During each calibration phase, the predictive model of each of the experts is trained on a sub-sequence of observation instants corresponding to the state with which it is associated, using an REW-NPLS (Recursive Exponentially Weighted N-way Partial Least Squares) regression model. A second predictive model giving the probability of occupancy of each state of the HMM model is also trained during (Continued)

each calibration phase using an REW-NPLS regression method. This second predictive model is used to calculate Markov mixture coefficients during a later operational prediction phase.

12 Claims, 3 Drawing Sheets

(51) Int. Cl.
  A61B 5/316 (2021.01)
  G06F 3/01 (2006.01)
  G06F 18/20 (2023.01)
  G06F 18/2113 (2023.01)
  G06F 18/214 (2023.01)
  G06N 7/01 (2023.01)
  G06N 20/20 (2019.01)

(52) U.S. Cl.
  CPC ........ *G06F 18/2113* (2023.01); *G06F 18/214* (2023.01); *G06F 18/295* (2023.01); *G06N 7/01* (2023.01); *G06N 20/00* (2019.01); *G06N 20/20* (2019.01)

(58) Field of Classification Search
  CPC ................ A61B 5/316; A61B 5/369; A61B 2560/0233; G06N 20/00; G06N 7/01; G06N 20/20
  See application file for complete search history.

(56) References Cited

OTHER PUBLICATIONS

French Preliminary Search Report issued Jun. 25, 2020 in French Application 1909706 filed on Sep. 4, 2019 (with English Translation of Categories of Cited Documents & Written Opinion), 10 pages.
Velliste et al., "Motor Cortical Correlates of Arm Resting in the Context of a Reaching Task and Implications for Prosthetic Control", The Journal of Neuroscience 34(17), 2014, pp. 6011-6022.
Srinivasan et al., "General-Purpose Filter Design for Neural Prosthetic Devices", Journal of Neurophysiology, 2007, pp. 2456-2475.
Eliseyev, et al., "Recursive Exponentially Weighted N-way Partial Least Squares Regression with Recursive-Validation of Hyper-Parameters in Brain-Computer Interface Applications", Scientific Reports, 2017, 15 pages.
U.S. Appl. No. 15/615,080, filed Jun. 6, 2017, U.S. Pat. No. 2018/0005105 A1, Schaeffer, M, et al.

* cited by examiner

ITERATIVE CALIBRATION METHOD FOR A DIRECT NEURAL INTERFACE USING A MARKOV MIXTURE OF EXPERTS WITH MULTIVARIATE REGRESSION

TECHNICAL FIELD

This invention relates to the field of direct neural interfaces also known as BCI (Brain Computer Interface) or BMI (Brain Machine Interface). Its applications are particularly direct neural control of a machine such as an exoskeleton or a computer.

STATE OF PRIOR ART

Direct neural interfaces use electrophysiological signals emitted by the cerebral cortex to generate a control signal. Much research has been made on these neural interfaces, particularly with the purpose of restoring a motor function to a paraplegic or tetraplegic patient using a prosthesis or a motor-driven orthosis.

Neural interfaces can have an invasive or a non-invasive nature. Invasive neural interfaces use intracortical electrodes (in other words implanted in the cortex) or cortical electrodes (positioned on the surface of the cortex), in the latter case collecting electrocorticographic (ECoG) signals. Non-invasive neural interfaces use electrodes placed on the scalp to collect electroencephalographic (EEG) signals. Other types of sensors have also been envisaged such as magnetic sensors measuring magnetic fields induced by the electrical activity of brain neurons. The term used in this case is magnetoencephalographic (MEG) signals.

Direct neural interfaces advantageously use ECoG type signals that have the advantage of providing a good compromise between biocompatibility (matrix of electrodes implanted on the surface of the cortex) and quality of the collected signals.

The ECoG signals thus measured must be processed so as to estimate the movement trajectory required by the patient and deduce control signals for the computer or the machine from these signals. For example, when the objective is to control an exoskeleton, the BCI interface estimates the required movement trajectory from the measured electrophysiological signals and uses them to deduce the control signals that will enable to exoskeleton to reproduce the trajectory in question. Similarly, when the objective is to control a computer, the BCI interface may for example estimate the required trajectory of a pointer or a cursor starting from electrophysiological signals and use them to deduce cursor/pointer control signals.

The estimate of the trajectory, and more precisely of the kinematic parameters (position, speed and acceleration), is also known as neural decoding in the literature. In particular, neural decoding can be used to control a movement (of a prosthesis or a cursor) from ECoG signals.

When the ECoG signals are acquired continuously, one of the main difficulties in decoding lies in the asynchronous nature of the control, in other words in the discrimination of phases during which the patient actually controls a movement (active period) and phases in which he does not control it (idle periods).

To circumvent this difficulty, direct neural interfaces called synchronous interfaces can only control a movement during well-defined time windows (for example periodically succeeding time intervals) signalled to the patient by an external index. The patient can then only control the movement during these time windows, but this proves to be unworkable in most practical applications.

More recently, direct neural interfaces with continuous decoding have been disclosed in the literature. The paper by M. Velliste et al. entitled "Motor cortical correlates of arm resting in the context of a reaching task and implications for prosthetic control" published in The Journal of Neuroscience, Apr. 23, 2014, 34 (17), pp. 6011-6022, describes in particular a direct neural interface in which idle state periods are detected by LDA (Linear Discriminant Analysis) making use of the action potentials emission frequency (neuron firing rate). Kinematic parameters are estimated during active periods by means of a state transition model, the states being predicted by a Laplacian of Gaussian filter. However, the results have been obtained for matrices of micro-electrodes and could not be reproduced for classical cortical electrodes. Furthermore, switchings between idle periods and active periods result in discontinuities in decoding the movement and therefore sudden changes along the trajectory.

Another approach has been proposed in the paper by L. Srinivasam et al. entitled "General-purpose filter design for neural prosthetic devices" published in J. Neurophysiol. Vol 98, pp. 2456-2475, 2007. This paper describes a direct neural interface with continuous decoding in which the sequence of active states and idle states is generated by a $1^{st}$ order Markov model. A Switching Kalman Filter or SKF for which the observation matrices and the transition matrices depend on the hidden switching variable (active state/idle state) can be used to estimate the kinematic parameters of the movement. This type of direct neural interface has been used to control a wheelchair making use of EEG signals based on simulation data but has not been tested for ECoG signals. Furthermore, detection of the state (active state/idle state) is sometimes incorrect (high rate of false positives and false negatives).

Finally, the above-mentioned direct neural interfaces have been developed to decode the movement of a single member of a patient. Therefore they are not adapted to the control of an exoskeleton with several members, particularly for a tetraplegic, paraplegic or hemiplegic patient, which significantly reduces their application field.

In the application published under number FR-A-3053495, it is proposed to decode the movement of several members by using a Markov mixture of experts or MME. This decoding is based on a Hidden Markov Model or HMM, an estimator (or expert) being associated with each hidden state of the model.

FIG. 1 schematically represents a BCI interface using a continuous movement decoding by a Markov mixture of experts.

This interface, 100, makes use firstly of a hidden state machine, 140, that can take K possible states, and secondly, a plurality K of estimators, 120, each estimator (or expert) being associated with a hidden state.

Estimates made by the different experts are combined in a combination module (gating network), 130, to give an estimate, $\hat{y}(t)$ of the variable to be explained, $y(t)$, in this case the kinematic movement parameters, starting from the observation $x(t)$ representing the characteristics of neural signals at time t, captured by means of electrodes 105. The sequence of observations $x[1:t]=\{x(1), x(2), \ldots, x(t)\}$ is modelled by a subjacent first order Markov process with continuous emission.

If the input variable $x(t)$ has dimension M and the response $y(t)$ has dimension N, and if the predictive models of the different experts $E_k$, are chosen to be linear, in other words $E_k(x(t))=\beta_k x(t)$ in which $\beta_k$ is a matrix with size N×M, the estimate by Markov mixture of experts is expressed as follows:

$$\hat{y}(t) = \sum_{k=1}^{K} g_k(t)\beta_k x(t) \quad (1)$$

in which $g_k(t)$ are weighting (or mixing) coefficients satisfying $$\sum_{k=1}^{K} g_k(t) = 1.$$

As indicated in the above-mentioned application, the parameters of the HMM model, in other words the probabilities of transition between hidden states, and the matrices $\beta_k$ can be estimated during a calibration phase, making use of a supervised estimating method. In this case, the HMM machine and the K experts are trained independently of each other. In particular, each expert $E_k$ can be trained on a sub-sequence of observations corresponding to the state k, the matrix $\beta_k$ of the predictive model then being estimated using a linear PLS (Partial Least Squares) regression starting from this sub-sequence.

More generally, the linear relation (1) can be extended to a multi-linear relation. The input variable can then be represented in tensor form $\underline{X} \in \mathbb{R}^{I_1 \times \cdots \times I_n}$ n in which n is the order of the input tensor and $I_i$ is the dimension of mode i.

Input tensor modes can for example be time (number of samples in time), frequency (number of spectral analysis bands), space (number of electrodes). Similarly, the response may be represented in tensor form $\underline{Y} \in \mathbb{R}^{J_1 \times \cdots \times J_m}$ in which m is the order of the output tensor. Output tensor modes can correspond to different effectors, for example acting on different joints of an exoskeleton.

Tensors of predictive models of the different experts can then be estimated by a multivariate PLS or NPLS (N-way PLS) method as described in the application published under number FR-A-3046471.

Regardless of which predictive models (PLS or NPLS) of the different experts are used, it has been observed that the validity duration of these models is relatively limited due to the lack of stationarity of signals in the human brain. Consequently, they have to be updated regularly by performing new calibration phases. However, a very large quantity of data has to be processed for each new calibration phase, combining data from previous calibrations and from the new calibration, for the different experts. The duration of the update is then often such that functioning of the direct neural interface has to be interrupted (off-line calibration). An iterative method of calibrating a direct neural interface based on an NPLS predictive model has thus been proposed in application FR-A-3061318. This iterative calibration method was also described in the paper written by A. Eliseyev et al. entitled "Recursive exponentially weighted N-way Partial Least Squares regression with recursive validation of hyper-parameters in Brain Computer Interface applications" published in Nature, Scientific Reports, volume 7, article number 16281, published on 24 Nov. 2017.

However, this iterative calculation method does not apply to a direct neural interface using a Markov mixture of experts as described in application FR-A-3046471.

One purpose of this invention is consequently to disclose a new method of calibrating a direct neural interface using a Markov mixture of experts, without needing to process a considerable quantity of data during each calibration phase, thus making operation of the direct neural interface possible in real time, without interruption.

PRESENTATION OF THE INVENTION

This invention is defined by a method of calibrating a direct neural interface according to the description in claim 1 in the set of claims given below. Advantageous embodiments are specified in the dependent claims.

BRIEF DESCRIPTION OF THE DRAWINGS

Other characteristics and advantages of the invention will become clear after reading a preferred embodiment of the invention, described with reference to the appended figures among which.

DETAILED PRESENTATION OF PARTICULAR EMBODIMENTS

Figure 1:
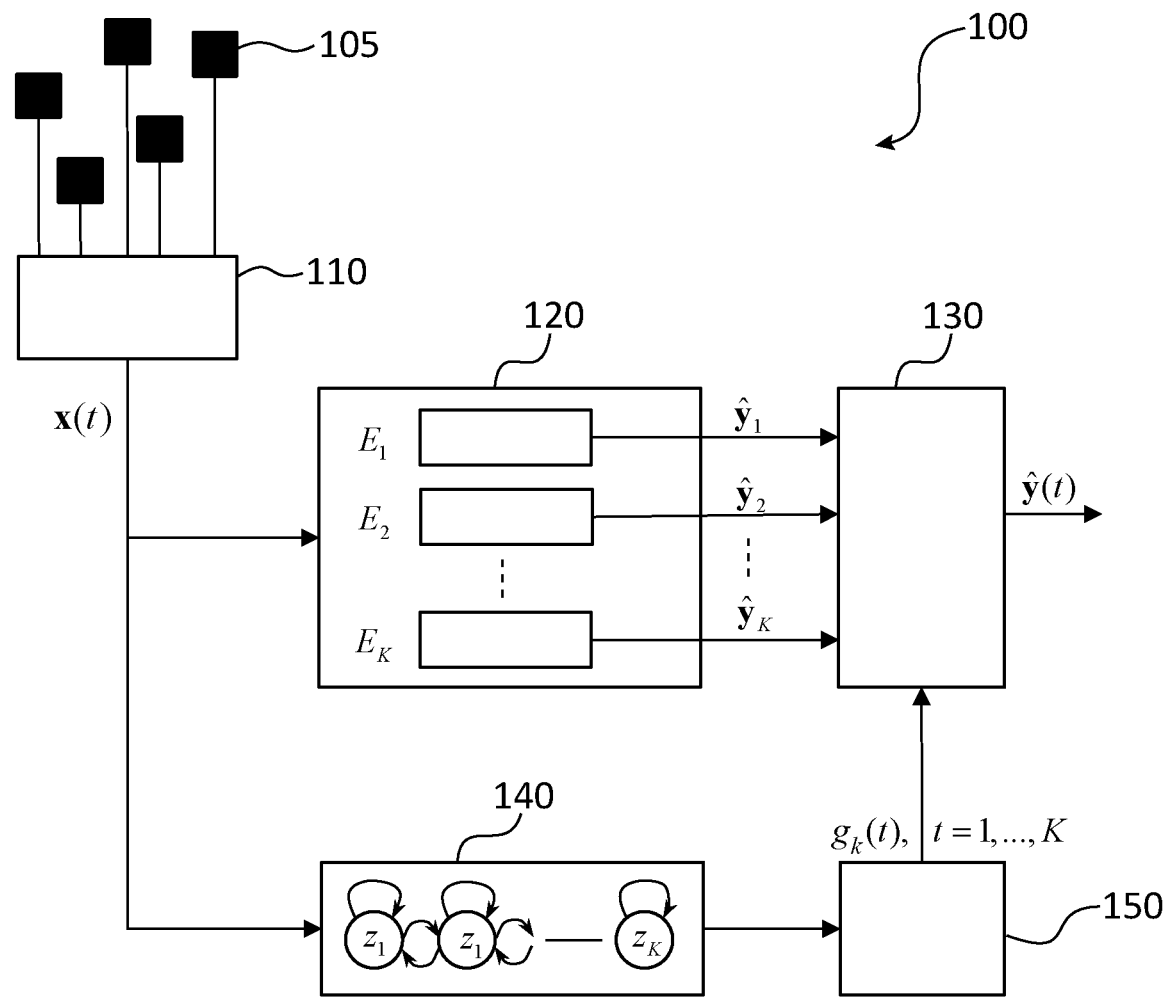
FIG. 1, described above, schematically represents a direct neural interface using a Markov mixture of experts, known in prior art.

In the following, we will consider a direct neural interface with continuous decoding using a Markov mixture of experts as described in the introductory part.

The electrophysiological signals output from the different electrodes are sampled and assembled by data blocks, each block corresponding to a sliding observation window with width $\Delta T$. For example, the electrophysiological signals are sampled at a frequency of about 590 kHz, and the size of data blocks is 590 samples ($\Delta T=1$ s), and the offset $\delta T$ from one observation window to the next is 59 samples ($\delta T=100$ ms). Each observation window is defined by an observation time (epoch) at which the window in question starts.

The electrophysiological signals are then preprocessed. In particular, this preprocessing may comprise elimination of the average taken on all electrodes, and a time-frequency analysis is then made on each observation window.

The time-frequency analysis can use a decomposition into wavelets, particularly Morlet wavelets.

A frequency smoothing or decimation can also be made on these results of the time-frequency analysis.

Thus, each observation window, or observation instant t, is associated with an order 3 tensor of observation data, resulting in the generation of an order 4 input tensor: the first mode corresponds to successive observation windows, the second mode corresponds to space, in other words the sensors, the third mode corresponds to time within an observation window, in other words the positions of the wavelets, and the fourth mode corresponds to the frequency, in other words to the number of frequency bands used for the decomposition into wavelets on an observation window.

More generally, the input tensor (or the observation tensor) will be order n+1, the first mode always being the mode relative to observation times (epochs). The input tensor (or observation tensor) is denoted $\underline{X}$ and its dimension is $N \times I_1 \times \ldots \times I_n$.

Similarly, the trajectory of the imagined movement, observed or performed, is described by an output tensor (or command tensor), order m+1, denoted $\underline{Y}$, with dimension $N \times J_1 \times \ldots \times J_m$, of which the first mode corresponds to successive times at which the commands will be applied (in general, this first mode also corresponds to the observation windows), the other modes corresponding to commands on the different effectors or different degrees of freedom of a multi-axis robot.

More precisely, the output tensor supplies N consecutive command data blocks, each of the blocks being used to generate command signals for the different effectors or degrees of freedom. Thus, it will be understood that the dimension of each data block can depend on the envisaged usage case and particularly on the number of degrees of freedom of the effector.

In the following, $\underline{X}_t$ will be used to denote the observation tensor at time t. Consequently, this tensor is order n and its dimension is $I_1 \times \ldots \times I_n$. It takes its values in a space $\underline{X} \subset \mathbb{R}^{I_1 \times \ldots \times I_n}$ in which $\mathbb{R}$ is the set of reals. Similarly, $\underline{Y}_t$ will be used to denote the command tensor at time t. Consequently, this output tensor is order m and dimension $J_1 \times \ldots \times J_m$. It takes its values in a space $\underline{Y} \subset \mathbb{R}^{J_1 \times \ldots \times J_m}$.

It will be assumed that the space $\underline{X}$ is formed from the union of a plurality K of regions, not necessarily discontiguous. In other words, $$X = \bigcup_{k=1}^{K} X_k$$

in which $X_k$, k=1, ..., K are the regions in question.

The direct neural interface is based on a mixture of experts (ME), each expert $E_k$ operating on the elementary region $X_k$ of the input characteristics space and being capable of predicting the command tensor $\underline{Y}_t$ at time t starting from the observation tensor, $\underline{X}_t$, when this tensor belongs to $X_k$. In other words, each region $X_k$ has a corresponding command tensor prediction model $\underline{Y}_t$ starting from the observation tensor $\underline{X}_t$. An expert $E_k$ can thus be considered as a multi-linear application of $X_k$ in $\underline{Y}$.

It will also be assumed that each expert $E_k$ is associated with a hidden state k of a first order Markov Model (HMM). The different experts are combined by means of combination coefficients dependent on the hidden state at the time of the prediction. Definitively, starting from an input (or observation) tensor $\underline{X}_t$, the neural interface estimates the output (or command) tensor $\underline{Y}_t$, using:

$$\hat{\underline{Y}}_t = \sum_{k=1}^{K} \gamma_k^t (\underline{\beta}_k \underline{X}_t + \underline{\delta}_k) \quad (2)$$

in which $\underline{\beta}_k$, $\underline{\delta}_k$ are a prediction coefficients tensor and an expert prediction bias tensor respectively, $E_k$ and $\delta_k^t$ is the weighting coefficient (also called the gating coefficient) for this expert and at the time t considered. The weighting coefficient $\gamma_k^t$ is simply the conditional probability that the HMM model is in the state k knowing the previous input tensors $\underline{X}_{1:t} = \underline{X}_1, \underline{X}_2, \ldots, \underline{X}_t$.

The set of coefficients and prediction biases, collectively called prediction parameters of the different experts, is designated by $\theta_e = \{(\underline{\beta}_k, \underline{\delta}_k) | k=1, \ldots, K\}$. The set of parameters for the combination of the different experts (including the parameters of the subjacent HMM model) is designated by $\theta_g = \{A, \{d_k | k=1, \ldots, K\}, \pi\}$ in which A is the transition matrix between states, with size K×K, in other words the matrix for which the elements $a^{ij}$ (independent of time by assumption of the HMM model) are defined by $a^{ij} = p(z_t = j | z_{t-1} = i)$ in which $z_t$ represents the state of the model at time t and $z_{t-1}$ represents the state of the model at the preceding time; $\{d_k | k=1, \ldots, K\}$ the parameters used to determine the conditional probability of observing the input tensor $\underline{X}_t$ knowing the state $z_t = k$, and $\pi$ is a vector with size K giving probabilities of occupancy of the different states at the initial time, in other words $\pi_i = p(z_t = i)_{t=0}$.

Figure 2:
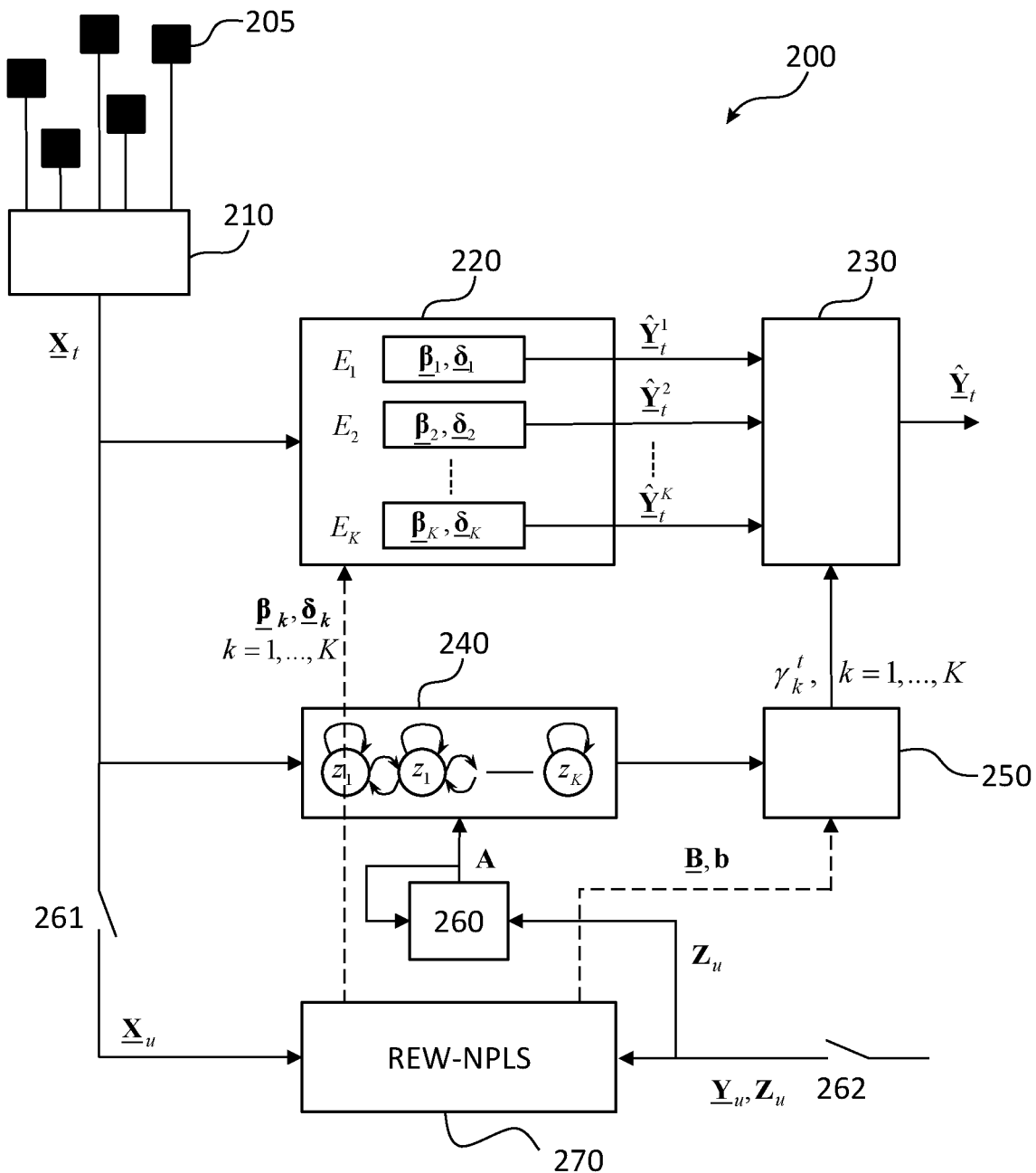
FIG. 2 schematically represents a direct neural interface using a Markov mixture of experts according to one embodiment of the invention.

FIG. 2 schematically represents a direct neural interface using a Markov mixture of experts according to one embodiment of the invention.

The electrophysiological signals output from the different electrodes 205 are processed in the processing module 210. This processing module performs sampling, optionally eliminates the average taken on all electrodes, and a time-frequency analysis is then made on each observation window. The time-frequency analysis can possibly be followed by frequency smoothing or decimation, as indicated above. Consequently, the processing module 210 outputs an input tensor $\underline{X}_t$ at each observation window, characterised by an observation time t.

The direct neural interface also makes use of a hidden state machine based on an HMM model, 240, that can be in K possible states, and a plurality of experts, 220, each expert being associated with a hidden state.

Each expert $E_k$ makes an estimate $\underline{Y}_t^k$ of the output vector $\underline{Y}_t$ and supplies it to a combination module, 230, that mixes the estimates according to expression (2). The combination coefficients (gating coefficients) are determined in the estimating module, 250, by $\gamma_k^t = p(z_t = k | \underline{X}_{1:t})$, k=1, ..., K, in which $z_t$ represents the state of the model at time t.

The estimate $\hat{\underline{Y}}_t$ gives the different kinematic movement parameters such as the position and/or the speed and/or the acceleration along the required trajectory.

The neural interface is calibrated firstly during an initialisation phase and then, during subsequent calibration phases, at given time intervals (on-line calibration).

These subsequent calibration phases are necessary due to the lack of stationarity of signals generated in the human brain. They can be done at regular intervals along the trajectory or successive trajectories to be executed.

A calibration phase u uses a plurality of input data blocks corresponding to a plurality $\Delta L$ of successive times output from the observation times sequence. $\underline{X}_u$ will denote the tensor with dimension $\Delta L \times I_1 \times \ldots \times I_n$ containing this plurality of input blocks. It also makes use of a plurality of output blocks giving kinematic set parameters, taken at the same times. $\underline{Y}_u$ will denote the set tensor with dimension $\Delta L \times J_1 \times \ldots \times J_m$ containing this plurality of input blocks.

The switches 261, 262 are in the closed position during a calibration phase. The calibration module 270 receives the input tensor $\underline{X}_u$, the set tensor $\underline{Y}_u$, and the matrix $Z_u$ with size $K \times \Delta L$, of which each of the columns represents the state of the machine at the time considered. More precisely, if at time $\ell$ the machine is in state $z\ell = k$, all elements in the $\ell^{th}$ column of the matrix $Z_u$ are null except for the element on row k that is equal to 1.

The calibration module uses $\underline{X}_u$, $\underline{Y}_u$, $\underline{Z}_u$ to calculate the updated parameter sets $\theta_e$ and $\theta_g$.

At the end of this calibration phase, the switches 261, 262 are open and the updated parameter sets $\theta_e$ and $\theta_g$ are output to a plurality of experts, 220, and to the machine 240, respectively.

Innovatively, the predictive model of each expert $E_k$ is trained using an REW-NPLS (Recursive Exponentially Weighted N-way Partial Least Squares) regression with a forget factor $\lambda^k$ ($0<\lambda^k<1$) on calibration data blocks, $\underline{X}_u$, $\underline{Y}_u$, corresponding to the hidden state $z_u=k$, denoted $\underline{X}_u^k$ and $\underline{Y}_u^k$. More precisely, for each expert $E_k$ and for each calibration phase u, the data blocks $\underline{X}_u^k$ and $\underline{Y}_u^k$ are determined so that it can be trained in a supervised manner.

This is done as described in application FR-A-3061318, namely:

In a first step, the tensors $\underline{X}_u^k$ and $\underline{Y}_u^k$ are normalised starting from a number of observations said to be effective $N_u^k = \lambda^k N_{u-1}^k + N_u^k$ in which $N_u^k$ is the number of data blocks corresponding to the hidden state $z_u=k$ during the calibration phase u. The weighted sum $s(\underline{X}_u^k)$ and the weighted quadratic sum $sq(\underline{X}_u^k)$ are calculated:

$$s(\underline{X}_u^k) = \lambda^k \sum_{\ell=1}^{N_{u-1}^k} x_{u-1;\ell,i_1,\ldots,i_n}^k + \sum_{\ell=1}^{N_u^k} x_{u;\ell,i_1,\ldots,i_n}^k \quad (3\text{-}1)$$

$$sq(\underline{X}_u^k) = \lambda^k \sum_{\ell=1}^{N_{u-1}^k} (x_{u-1;\ell,i_1,\ldots,i_n}^k)^2 + \sum_{\ell=1}^{N_u^k} (x_{u;\ell,i_1,\ldots,i_n}^k)^2 \quad (3\text{-}2)$$

in which $x_{u-1;\ell,i_1,\ldots,i_n}^k$ and $x_{u;\ell,i_1,\ldots,i_n}^k$ represent the elements of tensors $\underline{X}_{u-1}^k$ and $\underline{X}_u^k$, respectively. The average value $$\mu(\underline{X}_u^k) = \frac{s(\underline{X}_u^k)}{N_u^k}$$

and the standard deviation $$\sigma(\underline{X}_u^k) = \sqrt{\frac{sq(\underline{X}_u^k) - (\mu(\underline{X}_u^k))^2}{N_u^k}}$$

are then deduced. The elements of the centred and normalised input tensor, $\tilde{\underline{X}}_u^k$, are:

$$\tilde{x}_{u;\ell,i_1,\ldots,i_n}^k = \frac{x_{u;\ell,i_1,\ldots,i_n}^k - \mu(\underline{X}_u^k)}{\sigma(\underline{X}_u^k)} \quad (4)$$

Similarly, the weighted sum $s(\underline{Y}_u^k)$ and the weighted quadratic sum $sq(\underline{Y}_u^k)$ are calculated:

$$s(\underline{Y}_u^k) = \lambda^k \sum_{\ell=1}^{N_{u-1}^k} y_{u-1;\ell,j_1,\ldots,j_m}^k + \sum_{\ell=1}^{N_u^k} y_{u;\ell,j_1,\ldots,j_m}^k \quad (5\text{-}1)$$

$$sq(\underline{Y}_u^k) = \lambda^k \sum_{\ell=1}^{N_{u-1}^k} (y_{u-1;\ell,j_1,\ldots,j_m}^k)^2 + \sum_{\ell=1}^{N_u^k} (y_{u;\ell,j_1,\ldots,j_m}^k)^2 \quad (5\text{-}2)$$

The average value $$\mu(\underline{Y}_u^k) = \frac{s(\underline{Y}_u^k)}{N_u^k}$$

and the standard deviation $$\sigma(\underline{Y}_u^k) = \sqrt{\frac{sq(\underline{Y}_u^k) - (\mu(\underline{Y}_u^k))^2}{N_u^k}}$$

are then deduced, followed by the elements of the centred and normalised output tensor, $\tilde{\underline{Y}}_u^k$:

$$\tilde{y}_{u;\ell,j_1,\ldots,j_m}^k = \frac{y_{u;\ell,j_1,\ldots,j_m}^k - \mu(\underline{Y}_u^k)}{\sigma(\underline{Y}_u^k)} \quad (6)$$

The covariance tensor and the cross-covariance tensor are defined during the calibration phase u, starting from the centred and normalised tensors $\tilde{\underline{X}}_u^k$ and $\tilde{\underline{Y}}_u^k$:

$$\text{cov}(\tilde{\underline{X}}_u^k, \tilde{\underline{X}}_u^k) = \tilde{\underline{X}}_u^k \times_1 \tilde{\underline{X}}_u^k \quad (7\text{-}1)$$

$$\text{cov}(\tilde{\underline{X}}_u^k, \tilde{\underline{Y}}_u^k) = \tilde{\underline{X}}_u^k \times_1 \tilde{\underline{Y}}_u^k \quad (7\text{-}2)$$

in which $\times_1$ designates the tensor product according to the first mode (temporal mode with index $\ell$) as described in the above-mentioned application FR-A-3061318.

These covariance tensors are modified taking account of the covariance tensors of the previous calibration phase, by weighting them with the forget factor $\lambda^k$:

$$\text{cov}(\tilde{\underline{X}}_u^k,\tilde{\underline{X}}_u^k)=\lambda^k \text{cov}(\tilde{\underline{X}}_{u-1}^k,\tilde{\underline{X}}_{u-1}^k)+\tilde{\underline{X}}_u^k\times_1\tilde{\underline{X}}_u^k \quad (8\text{-}1)$$

$$\text{cov}(\tilde{\underline{X}}_u^k,\tilde{\underline{Y}}_u^k)=\lambda^k \text{cov}(\tilde{\underline{X}}_{u-1}^k,\tilde{\underline{Y}}_{u-1}^k)+\tilde{\underline{X}}_u^k\times_1\tilde{\underline{Y}}_u^k \quad (8\text{-}2)$$

This calculation takes account of the data from a previous calibration phase, with a forget factor, to update the covariance tensors. The forget factors relative to the different experts can be chosen to be identical $\lambda^k=\lambda$, $k=1,\ldots,K$, in which $\lambda$ is then the common forget factor. Alternatively, they can be chosen to be distinct so as to offer more prediction flexibility to the different experts.

Starting from the covariance tensors $\text{cov}(\tilde{\underline{X}}_u^k,\tilde{\underline{X}}_u^k)$ and $\text{cov}(\tilde{\underline{X}}_u^k,\tilde{\underline{Y}}_u^k)$ working iteratively on rank $f^k=1,\ldots,F$ in the latent variables space (in which F is a maximum predetermined number of dimensions in the latent variables space), we obtain a set of projection vectors $\{w_{u,1}^{k,f},\ldots,w_{u,n}^{k,f}\}_{f=1}^F$ with dimensions $I_1,\ldots,I_n$ respectively, a set of prediction coefficient tensors, $\{\underline{\beta}_u^{k,f}\}_{f=1}^F$, and a prediction bias sensor, $\{\underline{\delta}_u^{k,f}\}_{f=1}^F$, using the REW-NPLS method described in the above-mentioned application FR-A-3061318.

Starting from the covariance tensors $\text{cov}(\tilde{\underline{X}}_u^k,\tilde{\underline{X}}_u^k)$ and $\text{cov}(\tilde{\underline{X}}_u^k,\tilde{\underline{Y}}_u^k)$ working iteratively on rank $f^k=1,\ldots,F$ in the latent variables space (in which F is a maximum predetermined number of dimensions in the latent variables space), we obtain a set of projection vectors $\{w_{u,1}^{k,f},\ldots,w_{u,n}^{k,f}\}_{f=1}^F$ with dimensions $I_1,\ldots,I_n$ respectively, a set of prediction coefficient tensors, $\{\underline{\beta}_u^{k,f}\}_{f=1}^F$, and a prediction bias tensor, $\{\underline{\delta}_u^{k,f}\}_{f=1}^F$, using the REW-NPLS method described in the above-mentioned application FR-A-3061318.

The optimum rank, $f_{opt}^k$, for each expert $E_k$, during a calibration phase u is determined by calculating the prediction errors $\underline{Y}_u^k$ starting from $\underline{X}_u^k$ using the prediction coefficient tensors, $\{\underline{\beta}_u^{k,f}\}_{f=1}^F$, and the prediction bias tensors, $\{\underline{\delta}_u^{k,f}\}_{f=1}^F$ obtained during the previous calibration phase:

$$err_u^{k,f} = \lambda err_{u-1}^{k,f} + \|\underline{Y}_u^k - \hat{\underline{Y}}_{u-1}^{k,f}\| \quad (9)$$

in which $\hat{\underline{Y}}^{k,f}$ is the estimate of $\underline{Y}_u^k$ obtained from the prediction $\underline{\beta}_{u-1}^{k,f}$ and prediction bias coefficients $\underline{\delta}_{u-1}^{k,f}$ from the previous calibration phase.

The rank $f_{opt}^k$ leading to the minimum prediction error is then selected:

$$f_{opt}^k = \underset{f^k=1,\ldots,F}{\operatorname{argmin}} \left( err_u^{k,f^k} \right) \quad (10)$$

and for the calibration phase, the prediction coefficients tensor and the prediction bias tensor corresponding to this optimal rank are selected, in other words the update is made at the end of the calibration phase u:

$$\underline{\beta}_k = \underline{\beta}_u^{k,f_{opt}^k} \quad (11\text{-}1)$$

$$\underline{\delta}_k = \underline{\delta}_u^{k,f_{opt}^k} \quad (11\text{-}2)$$

for each of the experts $E_k$, $k=1, \ldots, K$, independently. The result obtained is thus an estimate of the set of prediction parameters $\theta_e$ making use of the REW-NPLS regression method applied to each of the experts.

Innovatively, the combination coefficients $\gamma_k^t$, $k=1, \ldots, K$ are also estimated using an REW-NPLS regression method adapted to discrete decoding, as described later.

During a calibration phase, the elements $a^{ij}$ of the transition matrix A are firstly updated as follows:

$$a_u^{ij} = \lambda a_{u-1}^{ij} + \frac{v_u^{ij}}{K} \quad (12)$$

in which $a_u^{ij}$ (or $a_{u-1}^{ij}$) are elements of the transition matrix, estimated during the calibration phase u (or u−1) and is the number of transitions from state i to state j during the calibration phase u. This number of transitions is obtained starting from the matrix $Z_u$. The lines in the transition matrix are then normalised such the sum of the probabilities of the transition from an initial state is equal to 1.

The transition matrix A thus updated is supplied by the transition matrix calculation module, 260, to the state estimating module, 240, of the HMM model.

$z_t$ defines a vector with size K for which the elements represent whether or not the machine is in state $k=1, \ldots, K$ at time t. Thus, if the machine is in state k at time t, only the kth element of $z_t$ will be equal to 1 and the other elements will be null. $z_t$ can be considered like a process with discrete values that vary in time according to a multilinear predictive model, the input variable of which is the observation tensor $\underline{X}_t$. This predictive model is trained under supervision during each calibration phase u, using the same principle as the predictive model of each expert. In other words:

$$\hat{z}_t = \underline{B}\underline{X}_t + b \quad (13)$$

in which $\hat{z}_t$ expresses the probabilities $\hat{z}_{k,t}$ that the machine is in state k at time t, $\underline{B}$ is a prediction coefficients tensor with size $K \times I_1 \times \ldots \times I_n$ and b is a bias vector with size K.

The tensor $\underline{B}$ and the vector b are updated during each calibration phase u by means of an REW-NPLS regression with a forget factor i $\lambda$, ($0 < \lambda < 1$) based on observations $\underline{X}_u$ and $Z_u$ (matrix with size $K \times \Delta L$). This forget factor may be identical to the common forget factor, when such a common forget factor is used to estimate prediction parameters for the different experts.

Working iteratively on rank $f=1, \ldots, F$ of the latent variables space starting from the covariance tensor cov($\tilde{\underline{X}}_u$, $\tilde{\underline{X}}_u$) in which $\tilde{\underline{X}}_u$ is a centred and normalised version of $\underline{x}_u$, and the cross-covariance tensor cov($\tilde{\underline{X}}_u$, $Z_u$). These covariance and cross-covariance tensors are modified by:

$$\operatorname{cov}(\tilde{\underline{X}}_u, \tilde{\underline{X}}_u) = \lambda \cdot \operatorname{cov}(\tilde{\underline{X}}_u, \tilde{\underline{X}}_u) + \tilde{\underline{X}}_u \times_1 \tilde{\underline{X}}_u \quad (14\text{-}1)$$

$$\operatorname{cov}(\tilde{\underline{X}}_u, Z_u) = \lambda \cdot \operatorname{cov}(\tilde{\underline{X}}_u, Z_u) + \tilde{\underline{X}}_u \times_1 Z_u \quad (14\text{-}2)$$

The REW-NPLS method provides a set of projection vectors $\{w_{u,1}, \ldots, w_{u,n}\}_{f-1}^F$, with dimensions $I_1, \ldots, I_n$ respectively, a set of prediction coefficient tensors, $\{\underline{\beta}_u^f\}_{f-1}^F$, and a set of prediction bias vectors, $\{b_u^f\}_{f-1}^F$. Rank $f_{opt}$ leading to the minimum prediction error is selected, then the tensor $\underline{B}$ and the vector b are updated by:

$$\underline{B} = \underline{B}_u^{f_{opt}} \quad (15\text{-}1)$$

$$b = b_u^{f_{opt}} \quad (15\text{-}2)$$

The tensor $\underline{B}$ and the vector b are supplied to the mixture coefficients estimating module, 250.

Starting from elements $\hat{z}_{k,t}$ of the predicted vector $\hat{z}_t$, the state estimating module can calculate the conditional probabilities using the softmax function:

$$p(z_t = k \mid \underline{X}_t) = \frac{\exp(\hat{z}_{k,t})}{\sum_{i=1}^K \exp(\hat{z}_{i,t})} \quad (16)$$

This expression gives the probability that the machine is in state k at time t, knowing the input data at this time.

The mixing coefficients estimating module, 250, obtains these coefficients from Bayes rule:

$$\gamma_k^t = p(z_t = k \mid \underline{X}_{1:t}) = \frac{p(z_t = k, \underline{X}_{1:t})}{p(\underline{X}_{1:t})} = \frac{p(z_t = k, \underline{X}_{1:t})}{\sum_{i=1}^K p(z_t = i, \underline{X}_{1:t})} \quad (17)$$

in which $p(z_t = i, \underline{X}_{1:t})$ are obtained using the forward algorithm, namely:

$$p(z_t = i, \underline{X}_{1:t}) = p(\underline{X}_t \mid z_t = i) \cdot \sum_{j=1}^K a^{ij} \gamma_k^{t-1} \quad (18)$$

The mixture coefficients can be obtained by recurrence by combining expressions (17) and (18):

$$\gamma_k^t = \frac{p(\underline{X}_t \mid z_t = k) \cdot \sum_{j=1}^K a^{kj} \gamma_k^{t-1}}{\sum_{i=1}^K \left( p(\underline{X}_t \mid z_t = i) \cdot \sum_{j=1}^K a^{ij} \gamma_i^{t-1} \right)} \quad (19)$$

The conditional emission probabilities, $p(\underline{X}_t|z_t=i)$ can be obtained using Bayes rule starting from a posteriori conditional probabilities $p(z_t=i|\underline{X}_t)$ and a priori probabilities $p(z_t=i|\underline{X}_t)$:

$$p(\underline{X}_t | z_t = i) = \frac{p(z_t = i | \underline{X}_t)p(\underline{X}_t)}{p(z_t = i)} \propto \frac{p(z_t = i | \underline{X}_t)}{p(z_t = i)} \quad (20)$$

the term $p(\underline{X}_t)$ being a multiplication coefficient common to all states.

The probabilities of occupancy of the different states $p(z_t=i)$ at time t are calculated from the initial probabilities of occupancy $\pi$ and the transition matrix A.

Figure 3:
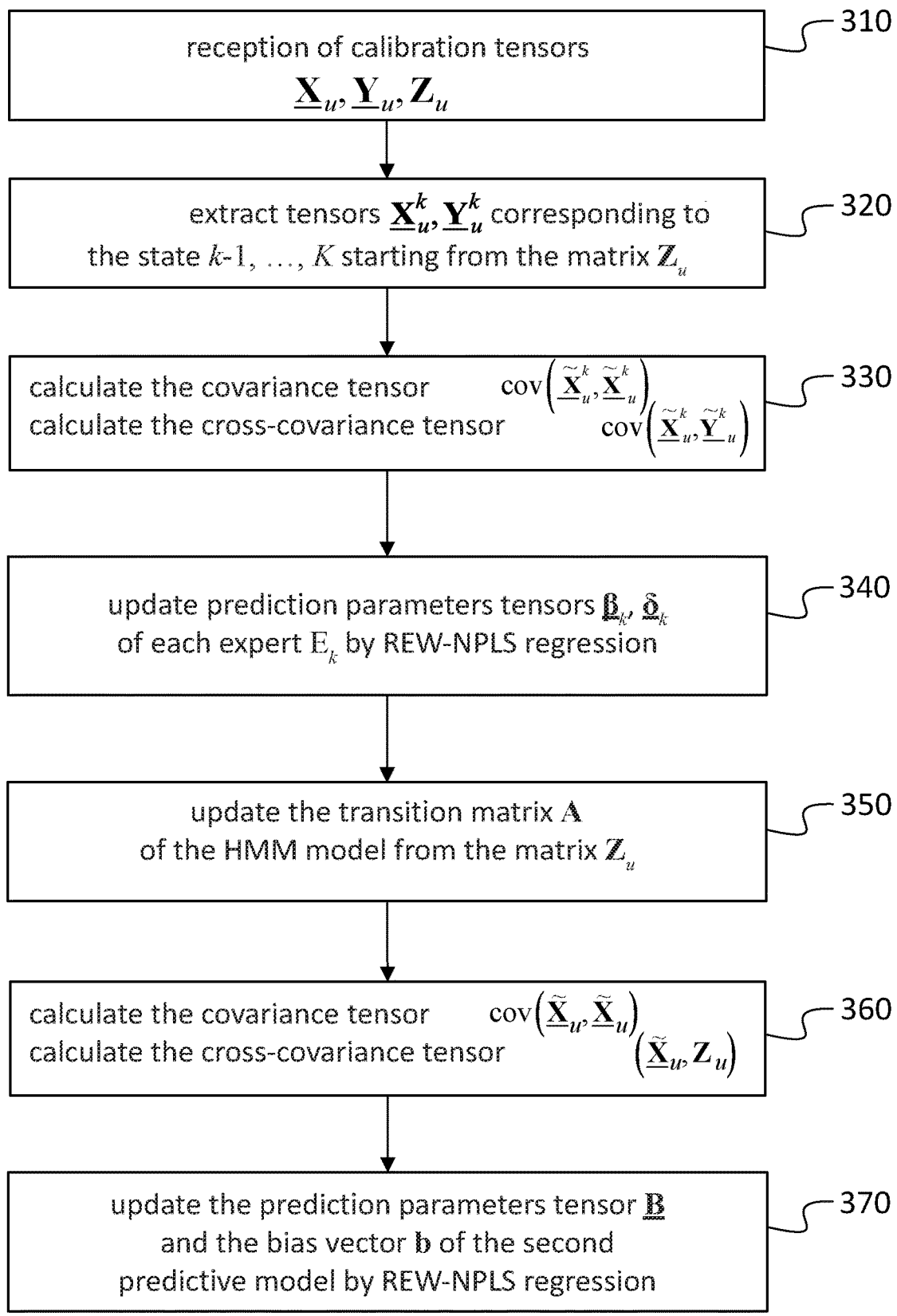
FIG. 3 is a flowchart representing a method of iteratively calibrating a direct neural interface using a Markov mixture of experts according to one embodiment of the invention.

FIG. 3 is a flowchart representing a method of iteratively calibrating a direct neural interface using a Markov mixture of experts according to one embodiment of the invention;

Said calibration method works during calibration phases planned at determined instants, for example at regular time intervals throughout the trajectory. Each calibration phase u uses a plurality of input data blocks corresponding to a plurality $\Delta L$ of successive times in the observation times sequence. It also makes use of a plurality of output blocks giving kinematic set parameters at the same times.

The plurality of input data blocks for the calibration phase u is represented by the input tensor $\underline{X}_u$ and the plurality of output blocks during this same calibration phase is represented by the output tensor $\underline{Y}_u$.

It is also assumed that the states of the HMM machine are known during the calibration phase. The different states of the HMM machine can relate to different elements to be controlled to make the trajectory, for example different members of an exoskeleton. Furthermore, for each of these elements, different states can be considered for example such as an active state when the patient controls this element, an idle state when he does not control it, and possibly a preparation state immediately preceding the active state and immediately following the idle state, during which the characteristics of the neural signals are not the same as in the idle state nor the active state for this element. Thus, when the direct neural interface must control P elements to make the trajectory, the HMM machine will comprise $2^P$ or even $3^P$ states (if preparatory states are envisaged). The states of the HMM machine during the calibration phase can be represented by a binary matrix $Z_u$ with size K×$\Delta L$, all values in each column in $Z_u$ being 0 except for one element equal to 1 indicating the state of the machine at the corresponding time.

The input tensor, $\underline{X}_u$, the output tensor, $\underline{Y}_u$, the states matrix, $Z_u$, are given in 310 for the calibration phase u.

In step 320, the matrix $Z_u$ is used as a starting point to determine the tensors $\underline{X}_u^k$ and $\underline{Y}_u^k$ formed by the input data blocks and the output data blocks related to the state k=1, ..., K, respectively. These tensors are extracted from the input tensor, $\underline{X}_u$, and the output tensor, $\underline{Y}_u$.

In step 330, for each expert $E_i$, k=1, ..., K the centred and normalised tensors $\tilde{\underline{X}}_u^k$ and $\tilde{\underline{Y}}_u^k$ are calculated and are used to deduce the covariance tensor $\tilde{\underline{X}}_u^k$, and the cross-covariance tensor of $\tilde{\underline{X}}_u^k$ and $\tilde{\underline{Y}}_u^k$. These tensors are modified by adding the covariance tensor of $\tilde{\underline{X}}_{u-1}^k$ and the cross-covariance tensor respectively, obtained in the previous calibration phase, weighted by a forget factor $\lambda^k$. These tensors thus modified will be used as covariance and cross-covariance tensors during the next calibration phase.

In step 340, the prediction parameter tensors $\underline{\beta}_k$, $\underline{\delta}_k$ of each expert $E_k$ are updated using an REW-NPLS regression, starting from the covariance and cross-covariance tensors modified in the previous step.

After step 340, we have an updated version of the set $\theta_e$ of expert prediction parameters K.

In step 350, the elements of the transition matrix A are advantageously updated starting from the number of transitions between successive states observed during the calibration phase u. The number of transitions between successive states is obtained starting from the matrix $Z_u$. The matrix A is then modified by adding to it the matrix A obtained during the previous iteration, weighted by a forget factor $\lambda$.

In step 360, the centred and normalised tensor $\tilde{\underline{X}}_u$ is added, followed by the covariance tensor of $\tilde{\underline{X}}_u$ and the cross-covariance tensor of $\tilde{\underline{X}}_u$ and $Z_u$. These tensors are modified by adding the covariance tensor of $\tilde{\underline{X}}_{u-1}^k$ and the cross-covariance tensor $\tilde{\underline{X}}_{u-1}^k$ and $Z_{u-1}$ respectively, obtained in the previous calibration, weighted by the forget factor $\lambda$. These tensors thus modified will be used as covariance and cross-covariance tensors during the next calibration phase.

In step 370, a multi-linear predictive model is trained giving a state vector of the HMM machine as a function of the input tensor, $\hat{z}_t = \underline{B}\underline{X}_t + b$, the components of the state vector $\hat{z}_t$ providing probabilities that the machine is in the different states k=1, ..., K respectively at time t. More precisely, the prediction parameter tensor $\underline{B}$, and the bias vector b are updated using an REW-NPLS regression, starting from the covariance and cross-covariance tensors modified in the previous step.

The components of $\hat{z}_t$ calculated during an operational phase are then used at each observation time t to obtain mixture coefficients $\gamma_k^t = p(z_t=k|\underline{X}_{1:t})$ of the different experts.

The invention claimed is:

1. A method of calibrating a direct neural interface that will receive a plurality of electrophysiological signals acquired using a plurality of sensors, during a plurality of observation windows associated with observation times, and provide command signals for one or more effectors configured to produce a trajectory or trajectories replicating a corresponding trajectory or trajectories of an imagined movement corresponding to one or more of the plurality of electrophysiological signals, said plurality of electrophysiological signals being preprocessed to obtain an observation tensor $(\underline{X}_t)$ at each observation time (t), changes in the observation tensor being modelled by a hidden Markov Model (HMM), said direct neural interface using a mixture of a plurality K of experts, each expert ($E_k$) being associated with a hidden state (k) of the HMM model and being defined by a multi-linear expert predictive model, comprising:
receiving the electrophysiological signals;
processing the electrophysiological signals to produce the observation tensor $(\underline{X}_t)$; and
calibrating during a plurality of calibration phases, at predetermined instants of said trajectory, each calibration phase (u) corresponding to a plurality ($\Delta L$) of successive observation times, and making use of a tensor $\underline{X}_u$ representing an observation tensor at said plurality ($\Delta L$) of successive times, a tensor $\underline{Y}_u$ representing a set of command tensors at these same times and a matrix $Z_u$, giving states of the HMM model at these same times, wherein each calibration phase comprises:
a step (a) in which tensors $\underline{X}_u$, $\underline{Y}_u$, are extracted using the matrix $Z_u$, observation tensors $\underline{X}_u^k$ and command tensors $\underline{Y}_u^k$, k=1, ..., K, relative to the different states (k) of the HMM model;
a step (b) in which the observation tensor is input to the plurality K of experts and, for, each expert $E_k$, tensors $\tilde{\underline{X}}_u^k$ and $\tilde{\underline{Y}}_u^k$ are calculated corresponding to tensors $\underline{X}_u^k$ and $\underline{Y}_u^k$ respectively, after being centred and normalised, then a covariance tensor of tensor $\tilde{\underline{X}}_u^k$ and a cross-covariance tensors of tensors $\tilde{\underline{X}}_u^k$ and $\tilde{\underline{Y}}_u^k$ being modified by adding covariance and cross-covariance tensors $\tilde{\underline{X}}_{u-1}^k$ and $\tilde{\underline{Y}}_{u-1}^k$ respectively derived from a previous calibration phase, weighted by a forget factor, $\lambda^k$;

a step (c) of using a multivariate regression of partial least squares with exponential recursive weighting (REW-NPLS) regression, starting from covariance and cross-covariance tensors modified in the previous step to generate prediction coefficient tensors and a prediction bias tensor which are input to the linear predictive expert models for training the linear predictive expert models, thereby updating the linear predictive expert models;

a step (d) in which the tensor $\tilde{\underline{X}}_u$ corresponding to the tensor $\underline{X}_u$, after being centred and normalised, the covariance tensor of tensor $\tilde{\underline{X}}_u$ and the cross-covariance tensor of $\tilde{\underline{X}}_u$ and $Z_u$ are calculated, the covariance tensor of tensor $\tilde{\underline{X}}_u$ and cross-covariance tensor of $\tilde{\underline{X}}_u$ and $Z_u$ being modified by adding to them the covariance tensor of $\tilde{\underline{X}}_{u-1}$ and the cross-covariance tensor of $\tilde{\underline{X}}_{u-1}$ and $Z_{u-1}$, derived from the previous calibration phase, weighted by a forget factor $\lambda$;

a step (e) of training a second multi-linear predictive model using an REW-NPLS regression starting from covariance and cross-covariance tensors modified in the previous step to generate a prediction coefficients tensor and a bias vector which are input to the second multi-linear predictive model, thereby updating the second multi-linear predictive model to give a state vector ($\hat{z}_t$) of the HMM model as a function of the centred and normalised input tensor, $\tilde{\underline{X}}_u$, components of the state vector providing possibilities that the direct neural interface is in each of the different states k=1, . . . ,K at an observation time, and generating mixture coefficients ($v_k^t$, k=1, . . . ,K) of different experts using the second multi-linear predictive model; and a step (f) of providing an estimate ($\hat{\underline{Y}}_t$) of a control tensor representing the command signals.

2. The method of calibrating the direct neural interface according to claim 1, wherein in each calibration phase, a number of transitions is determined for each pair of states observed during this calibration phase, and the transition matrix of the HMM model is updated using these numbers and the transition matrix of the HMM model calculated during the previous calibration phase, weighted by a forget factor.

3. The method of calibrating the direct neural interface according to claim 1, wherein in step (b), a modified covariance tensor cov($\tilde{\underline{X}}_u^k, \tilde{\underline{X}}_u^k$) of the observation tensor for state k, centred and normalised, $\tilde{\underline{X}}_u^k$, is calculated by cov($\tilde{\underline{X}}_u^k, \tilde{\underline{X}}_u^k$)=$\lambda^k$ cov($\tilde{\underline{X}}_{u-1}^k, \tilde{\underline{X}}_{u-1}^k$)+$\tilde{\underline{X}}_u^k \times \tilde{\underline{X}}_u^k$ in which $\times_1$ is a tensor product for a first mode, and in that the modified cross-covariance tensor cov($\tilde{\underline{X}}_u^k, \tilde{\underline{Y}}_u^k$) in which $\tilde{\underline{Y}}_u^k$ is a command tensor related to the centred and normalised state k is calculated by cov($\tilde{\underline{X}}_u^k, \tilde{\underline{Y}}_u^k$)=$\lambda^k$ cov($\tilde{\underline{X}}_{u-1}^k, \tilde{\underline{Y}}_{u-1}^k$)+$\tilde{\underline{X}}_u^k \times_1 \tilde{\underline{Y}}_u^k$.

4. The method of calibrating the direct neural interface according to claim 3, wherein in step (c), for each expert $E_k$, k=1, . . . , K, an optimal rank, $f_{opt}^k$, in a latent variables space for the REW-NPLS regression is determined as that which minimises an error $err_u^{k,f}=\lambda^k\ err_{u-1}^{k,f}+\|\underline{Y}_u^k-\hat{\underline{Y}}_{u-1}^{k,f}\|$ in which $err_u^{k,f}$ is a prediction error of the command tensor related to state k, by the expert $E_k$ during the calibration phase u for a rank $f_k=1, \ldots, F$ in which F is a predetermined maximum rank, and $\hat{\underline{Y}}_{u-1}^{k,f}$ is a prediction of $\underline{Y}_u^k$ by the expert $E_k$, obtained by the multi-linear predictive model of the same expert during the previous calibration phase, for the same rank.

5. The method of calibrating the direct neural interface according to claim 1, wherein in step (d), a modified covariance tensor cov($\tilde{\underline{X}}_u, \tilde{\underline{X}}_u$) of the observation tensor, centred and normalised, $\tilde{\underline{X}}_u$, is calculated by cov($\underline{X}_u,\underline{X}_u$)=$\lambda$cov($\underline{X}_u,\underline{X}_u$)+$\underline{X}_u\times_1\underline{X}_u$ in which $\times_1$ is a tensor product for a first mode, and in that the cross-covariance tensor cov($\tilde{\underline{X}}_u,Z_u$) is modified by cov($\underline{X}_u,Z_u$)=$\lambda$cov($\underline{X}_u,Z_u$)+$\underline{X}_u\times_1 Z_u$.

6. The method of calibrating the direct neural interface according to claim 5, wherein in step (e), an optimal rank, $f_{opt}$, in a latent variables space for the REW-NPLS regression is determined as that which minimises an error $err_u^f=\lambda err_{u-1}^f+\|\underline{Y}_u-\hat{\underline{Y}}_{u-1}^f\|$ in which err/is a prediction error of the command tensor during the calibration phase u for a rank f=1, . . . , F in which F is a predetermined maximum rank, and $\hat{\underline{Y}}_{u-1}^f$ is a prediction of $\underline{Y}_u$ by a mixture of experts weighted by mixture coefficients obtained by the second multi-linear predictive model during the previous calibration phase, for the same rank.

7. The method of calibrating the direct neural interface according to claim 1, wherein the plurality of electrophysiological signals are electrocorticographic signals.

8. The method of calibrating the direct neural interface according to claim 1, comprising:

a step (g) of outputting a signal representing the estimate ($\hat{\underline{Y}}_t$) corresponding to different kinematic movement parameters including at least one of position, speed and acceleration along the trajectory.

9. The method of calibrating the direct neural interface according to claim 1, comprising:

a step (g) of outputting a signal representing the estimate ($\hat{\underline{Y}}_t$) corresponding to different kinematic movement parameters including at least one of position, speed and acceleration of a multi-axis robot.

10. The method of calibrating the direct neural interface according to claim 1, wherein the plurality of calibration phases are conducted at regular intervals through the trajectory.

11. The method of calibrating the direct neural interface according to claim 1, comprising a step (g) of using the generated mixture coefficients ($\lambda_k^t$, k=1, . . . , K) and the predictions generated by the experts to generate a signal representing the estimate ($\hat{\underline{Y}}_t$) of a control tensor representing the command signals.

12. The method of calibrating the direct neural interface according to claim 1, comprising extracting $\underline{X}_u$ as a plurality of data blocks and producing N command data blocks corresponding to the command signals.

* * * * *